United States Patent
Glasky et al.

(10) Patent No.: US 8,377,456 B2
(45) Date of Patent: *Feb. 19, 2013

(54) METHODS FOR TREATING COGNITIVE/ATTENTION DEFICIT DISORDERS USING TETRAHYDROINDOLONE ANALOGUES AND DERIVATIVES

(75) Inventors: Alvin J. Glasky, Mission Viejo, CA (US); David B. Fick, Tustin, CA (US); David R. Helton, Irvine, CA (US)

(73) Assignee: Spectrum Pharmaceuticals, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/246,014

(22) Filed: Sep. 27, 2011

(65) Prior Publication Data

US 2012/0070385 A1     Mar. 22, 2012

Related U.S. Application Data

(63) Continuation of application No. 12/414,539, filed on Mar. 30, 2009, now Pat. No. 8,063,233, which is a continuation of application No. 11/002,329, filed on Dec. 1, 2004, now Pat. No. 7,531,670, which is a continuation of application No. 10/193,550, filed on Jul. 9, 2002, now Pat. No. 6,982,269, which is a continuation-in-part of application No. 09/839,289, filed on Apr. 20, 2001, now Pat. No. 6,759,427.

(51) Int. Cl.
*A61K 47/00* (2006.01)
*C07D 209/14* (2006.01)

(52) U.S. Cl. ........ 424/400; 424/424; 424/426; 424/489; 548/469

(58) Field of Classification Search .......... 424/426–484, 424/400, 489; 548/449, 469
See application file for complete search history.

(56) References Cited

U.S. PATENT DOCUMENTS

| | | |
|---|---|---|
| 3,300,380 A | 1/1967 | Glasky et al. |
| 3,321,369 A | 5/1967 | Glasky et al. |
| 3,438,968 A | 4/1969 | Glasky et al. |
| 3,666,856 A | 5/1972 | Elion et al. |
| 4,035,486 A | 7/1977 | Laborit |
| 4,138,562 A | 2/1979 | Vince |
| 4,221,794 A | 9/1980 | Simon et al. |
| 4,221,909 A | 9/1980 | Simon et al. |
| 4,221,910 A | 9/1980 | Giner-Sorolla |
| 4,315,920 A | 2/1982 | Schaeffer et al. |
| 4,340,726 A | 7/1982 | Simon et al. |
| 4,347,360 A | 8/1982 | Ogilvie |
| 4,451,478 A | 5/1984 | Simon et al. |
| 4,643,992 A | 2/1987 | Goodman et al. |
| 4,952,693 A | 8/1990 | Sircar et al. |
| 4,977,178 A | 12/1990 | Howard et al. |
| 5,023,244 A | 6/1991 | Goto et al. |
| 5,091,432 A | 2/1992 | Glasky |
| 5,093,318 A | 3/1992 | Goodman et al. |
| 5,187,162 A | 2/1993 | Marangos et al. |
| 5,237,051 A | 8/1993 | Garbers et al. |
| 5,256,677 A | 10/1993 | Sham et al. |
| 5,376,642 A | 12/1994 | Yarchoan et al. |
| 5,447,939 A | 9/1995 | Glasky |
| 5,565,437 A | 10/1996 | Marquez et al. |
| 5,595,901 A | 1/1997 | Rocancourt et al. |
| 5,646,300 A | 7/1997 | Kosley, Jr. et al. |
| 5,795,756 A | 8/1998 | Johnson et al. |
| 5,801,159 A | 9/1998 | Miller et al. |
| 5,801,184 A | 9/1998 | Glasky et al. |
| 5,948,771 A | 9/1999 | Danziger |
| 6,027,936 A | 2/2000 | Glasky |
| 6,630,478 B2 | 10/2003 | Diamond et al. |
| 6,630,490 B2 | 10/2003 | Diamond et al. |
| 6,759,427 B2 * | 7/2004 | Fick et al. ............ 514/415 |
| 6,770,638 B2 * | 8/2004 | Fick et al. ............ 514/183 |
| 6,982,269 B2 * | 1/2006 | Glasky et al. ......... 514/418 |
| 7,531,670 B2 * | 5/2009 | Glasky et al. ......... 548/469 |
| 7,795,266 B2 * | 9/2010 | Helton et al. ......... 514/254.09 |
| 8,063,233 B2 * | 11/2011 | Glasky et al. ......... 548/469 |
| 2002/0040031 A1 | 4/2002 | Glasky et al. |
| 2002/0040032 A1 | 4/2002 | Glasky et al. |
| 2002/0128264 A1 | 9/2002 | Taylor |
| 2002/0198218 A1 | 12/2002 | Fick et al. |

FOREIGN PATENT DOCUMENTS

| | | |
|---|---|---|
| EP | 754681 | 1/1997 |
| WO | 99/56550 | 11/1999 |
| WO | 99/57119 | 11/1999 |
| WO | 99/57120 | 11/1999 |
| WO | 99/62899 A1 | 12/1999 |
| WO | WO 9962899 A1 * | 12/1999 |
| WO | 01/77075 A2 | 10/2001 |
| WO | 02/04448 A2 | 1/2002 |

OTHER PUBLICATIONS

A. Aurell et al., "The S-100 Protein in Cerebrospinal Fluid: A Simple ELISA Method," J.Neurol. Sci. 89:157-164 (1989).
A. Dhainaut et al., "New Purines and Purine Analogs as Modulators of Multi-Drug Resistance," J. Med. Chem. 39:4099-4108 (1996).
A. Nitta et al., "Effects of Oral Administration of a Stimulator for Nerve Growth Factor Synthesis in Basal Forebrain-Lesioned Rats," Eur. J. Pharmacol. 250:23-30 (1993).
A. Seiger et al., "Intracranial Infusion of Purifide Nerve Growth Factor to an Alzheimer Patient: The First Attempt of a Possible Future Treatment Strategy," Behavioural Brain Res. 57:255-261 (1993).
A. Verma et al., "Carbon Monoxide: A Putative Neural Messenger," Science 249:381-384 (1993).
A. Yamazaki et al., Synthesis of Guanosine and Its Derivatives from 5-Amino-1β-D-Ribofuranosyl-4-Imidazolecarboxamide I, Ring Closure with Benzoyl Isothiocyanate, J. Org. Chem. 32:1825-1828 (1967).

(Continued)

*Primary Examiner* — Michael G Hartley
*Assistant Examiner* — Micah-Paul Young
(74) *Attorney, Agent, or Firm* — K&L Gates LLP; Louis C. Cullman; Dean G. Stathakis

(57) ABSTRACT

The present specification discloses tetrahydroindolone derivatives or analogues and methods for treating cognitive/attention deficit disorders using such tetrahydroindolone derivatives and analogues.

26 Claims, 1 Drawing Sheet

OTHER PUBLICATIONS

A.D. Mooradian, "Effect of Aging on the Blood-Brain Barrier," Neurbiol. Aging 9: 31-39 (1988).

A.E. Miller et al., "Immunological Studies in Senile Dementia of the Alzheimer Type: Evidence for Enhanced Suppressor Cell Activity," Ann. Neurol. 10:506-510 (1981).

A.G. Gittis & J.R. Puzuasky, "AIT-082 Improves Memory Performance in a Non-Match-to-Sample Task in Rats," Soc. Neurosci. 25: 62 (1999) (abstract).

A.J. Glasky et al., "Effect of AIT-082, a Purine Analog, on Working Memory in Normal and Aged Mice," Pharmacol. Biochem. Behav. 47: 325-329 (1994).

A.J. Glasky et al., "Neurotrophins, Growth Factors and Mimetic Agents as Neuroprotectors in the Treatment of Alzheimer's Disease" in Alzheimer Disease: From Molecular Biology to Therapy (R. Becker & E. Giacobini, eds., Birkhäuser, Boston, 1996), pp. 119-124.

A.L. Betz, "Identification of Hypoxanthine Transport and Xanthine Oxidase Activity in Brain Capillaries," J. Neurochem. 44:574-579 (1985).

B. Alhede et al., "A Simple and Efficient Synthesis of 9-Substituted Guanines. Cyclodesulfurization of 1-Substituted 5-[(Thiocarbamoyl)amino]imidazole-4-carboxamides under Aqueous Basic Conditions," J. Org. Chem. 56:2139-2143 (1991).

B.H.J. Juurlink et al., "The Hypoxanthine Analogue AIT-082 Promotes Neurite Formation and Regeneration in Cultured Hippocampal Neurons," Soc. Neurosci. 24: 1941 (1998) (abstract).

D. Manetti et al., "Design, Synthesis, and Preliminary Pharmacological Evaluation of 1,4-Diazabicyclo[4,3.0] nonan-9-ones as a New Class of Highly Potent Nootropic Drugs," J. Med. Chem. 43: 1969-1974 (2000).

D. Manetti et al., "Molecular Simplification of 1,4-Diazabicyclo[4,3. 0]nonan-9-ones Given Piperazine Derivatives That Maintain High Nootropic Activity," J. Med. Chem. 43: 4499-4507 (2000).

D. Triguero et al., "Capillary Depletion Method for Quantitation of Blood-Brain Barrier Transport of Circulating Peptides and Plasma Proteins," J. Neurochem, 54: 1882-1888 (1990).

D.A. Nugiel et al., "Facile Preparation of 2,6-Disubstituted Purines Using Solid Phase Chemistry," J. Org. Chem.J. Org. Chem. 62:201-203 (1997).

D.B. Fick et al., Discovery and development of NEO-339, a compound that increases attentional processes associated with improvement in cognition. 28th National Medicinal Chemistry Symposium, San Diego, CA Jun. 8-12, 2002.

D.H. Maurice & R.J. Haslam, "Molecular Basis of the Synergistic Inhibition of Platelet Function by Nitrovasodilators and Activators of Adenylate Cyclase: Inhibition of Cyclic AMP Breakdown by Cyclic GMP," Mol. Pharmacol. 37:671-681 (1990).

D.L. Temple, JRL, "Substituted 6,7-Dihydroimidazo[1.2-a] Purin-9 (4H)-ones," J. Med Chem. 23:1188-1198 (1980).

D.R. Helton et al., NEO-339, a novel therapeutic agent for the treatment of mild cognitive impairment and attention deficits. XIVth World Congress of Pharmacology, San Franciso, CA Jul. 7-12, 2002.

D.R. Helton, R.F. Ritzman, V. Fedulov, J.R. Smith, M.M. Foreman, A.J. Glasky, "Effect of NEO-339 on Learning, Memory, and Sensorimotor Responsiveness in Young and Aged Mice," Abstract 78. 17, 31st Annual Meeting of the Society for Neuroscience, San Diego, CA, Nov. 10-15, 2001.

E.G. G Gutierrez et al., "Murine Tumor Necrosis Factor Alpha Is Transported from Blood to Brain in the Mouse," J. Neuroimmunol. 47: 169-176 (1993).

E.M. Cornford & W.H. Olendorf, "Independent Blood-Brain Barrier Transport Systems for Nucleic Acid Precursors," Biochim. Biophys. Acta 394: 211-219 (1975).

E.M. Taylor et al., "14C-AIT082 Crosses the Blood-Brain Barrier and Is Pumped Out of Brain by a Probenecid- and Verapamil-Sensitive Mechanism," Soc. Neurosci. 25: 1758 (1999) (abstract).

F. Caciagli et al., "The Hypoxanthine Analogue AIT-082 Mimics the Activity of Guanosine in Affecting Extracellular Adenosine Breakdown and Glutamate Reuptake in Rat Cultured Astrocytes," Soc. Neurosci. 25: 1195 (1999) (abstract).

F. Caciagli et al., "The Hypoxanthine Derivative AIT-082 Protects Against Neurotoxicity in Vitro and in Vivo," Soc. Neurosci. 24: 1941 (1998) (abstract).

F. Zaragoza Dorwald; Side Reactions in Organic Synthesis, 2005, Wiley-VCH Vedag Gmbh & Coi. KGaA, Weinheim; ISBN 3-527-310231-5; Preface.

F.G. Blasberg et al., "Transport of a-Aminoisobutyric Acid Across Brain Capillary and Cellular Membranes," J. Cereb. Blood Flow Metab. 3: 8-32 (1983).

G. Shaw et al., "Purines, Pyrimidines, and Glyoxalines. Part XIII. Some New Unambiguous Syntheses of 5-Aminoglyoxalines and 5-Aminoglyoxaline-4-carboxamides, and a Synthesis of 5-Amino-1-β-D-ribofuranosylglyoxaline-4-carboxyamide," J. Chem. Soc. 1959: 1648- (1959).

G.A. Lyles & B.A. Callingham, "The Effects of Thyroid Hormones on Monoamine Oxidase in the Rat Heart," J. Pharm. Pharmacol, 26:921-930 (1974).

G.M. Blackburn & M.J. Gait, eds., Nucleic Acids in Chemistry and Biology (2d ed., Oxford University press, 1996), pp. 148-152.

G.N. Shah & A.D. Mooradian, "Age-Related Changes in the Blood-Brain Barrier," Exp. Gerontol. 32: 501-519 (1997).

I. Skoog et al., "A Population Study on Blood-Brain Barrier Function in 85-Year-Olds: Relation to Alzheimer's Disease and Vascular Dementia," Neurology 50: 966-971 (1998).

I.D. Laviada et al., :Phosphatidylcholine-Phospholipase C. Mediates the Induction of Nerve Growth Factor in Cultured Glial Cells, FEBS Lett. 364:301-304 (1995).

J. Barnett et al., "Human β Nerve Growth Factor Obtained from a Baculovirus Expression System Has Potent in Vitro and in Vivo Neurotrophic Activity," Exp. Neurol. 110:11-24 (1990).

J.E. Savelli et al., "Modulation of N-Methyl-D-Aspartate (NMDA) Antagnoist-Induced Darting Behaviour by the Peptidomimetic PAMTA," Brain Res. 682:41-49 (1995).

J.F. Poduslo & G.L. Curran, "Permeability at the Blood-Brain Barrier and Blood-Nerve Barriers of the Neurotrophic Factors: NGF, CNTF, NT-3 BDNF," Mol. Brain Res. 36: 280-286 (1996).

J.F. Poduslo et al., "Macromolecular Permeability Across the Blood-Nerve and Blood-Brain Barriers," Proc. Natl. Acad. Sci. USA 91: 5705-5709 (1994).

J.J. Ramirez et al., "AIT-082 Accelerates Septodentate Sprouting AFter Unilateral Entorhinal Cortex Lesion in Rats," Soc. Neurosci. Abstr. 24: 1942 (1998).

J.S. Bintner et al., "AIT 082, a Hypoxanthine Derivative, Prevents Much of the Decrease in Cerebellar Neuron ATP Following Glutamate Exposure," Soc. Neruosci. 25: 2131 (1999) (abstract).

J.Z. Fields et al., "Cardiac Muscarinic Cholinergic Receptors: Biochemical Identification and Characterization," J. Biol. Chem. 253:3251-3258 (1978).

K. Nagarajan et al., Synthesis and oral hypoglycemic properties of 4-oxo-4,5,6,7-tetrahydroindole-3-acetic acids. Chemical Abstracts, 1998, vol. 111, Columbus, Ohio.

K. Stefansson, "Neuroimmunology of Aging" in Clinical Neurology of Aging (M.L. Albert, ed., Oxford University Press, Oxford, (1984)), ch. 4. pp. 76-94.

K.A. Jacobson, "Chemical Approaches to the Definition of Adenosine Receptors" in Adenosine Receptors (D.M.F. Cooper & C. Londos, eds., Receptor Biochemistry and Methodology, J.C. Venter, L.C. Harrison, eds., Alan R. Liss: New York, 1988), pp. 11:1-26.

K.G. Estep et al., "Synthesis and Structure-Activity Relationships of 6-Heterocyclic-Substituted Purines as Inactivation Modifiers of Cardiac Sodium Channels," J.Med. Chem. 38:2582-2595 (1995).

K.L. Audus et al., "Brain Uptake of Drugs: the Influence of Chemical and Biological Factors," Adv. Drug Res. 23:1-64 (1992).

L.R. Weitkamp et al., "Alzheimer Disease: Evidence for Susceptibility Loci on Chromosomes 6 and 14," Am. J. Hum. Genet. 35:443-53 (1983).

M. Barinaga, "Carbon Monoxide: Killer to Brain Messenger in One Step," Science 259:309 (1993).

M. Hosokawa & J. Ueno, "Aging of Blood-Brain Barrier and Neuronal Cells of Eye and Ear in SAM Mice," Neurobiol. Aging 20: 117-123 (1999).

M. Iwakawa et al., "Synthetic Routes to Nucleoside Analogs of N-Substituted 1,3-Thiazolidines," Can J. Chem 56:326-335 (1978).

M. Zuo et al., "Nitric Oxide and Carbon Monoxide Produce Activity-Dependent Long-Term Synaptic Enhancement in Hippocampus," Science 260: 1946-1950 (1993).

M.D. Johnson & B.D. Anderson, "Localization of Purine Metabolizing Enzymes in Bovine Brain Microvessel Endothelial Cells: An Enzymatic Blood-Brain Barrier for Dideoxynucleosides?," Pharm. Res. 13: 1881-1886 (1996).

M.H. Tuszynski & F.H. Gage, "Neurotrophic Factors and Neuronal Loss," in Alzheimer Disease (R.D. Terry et al., eds, Raven Press, New York, 1994), ch. 25, pp. 405-417.

M.L. Peterson & R. Vince, "Synthesis and Biological Evaluation of 4-Purinylpyrrolidine Nucleosides," J. Med. Chem. 34:2787-2795 (1991).

M.M. Bradford, "A Rapid and Sensative Method for the Quantitation of Microgram Quantities of Protein Using the Principle of Protein-Dye Binding," Anal. Biochem. 72:248-254 (1976).

M.P. Rathbone et al., AIT-082 as a Potential Neuroprotective and Regenerative Agent in Stroke and Central Nervous System Injury, Exp. Opin. Invest. Drugs 8: 1255-1262 (1999).

M.P. Rathbone et al., "Physiology and Pharmacology of Natural and Synthetic Nonadenine Based Purines in the Nervous System," Drug Develop. Res. 45: 356-372 (1998).

N.W. Tietz, ed., "Textbook of Clinical Chemistry" (W.B. Saunders Co., Philadelphia, 1986), pp. 882-886.

O. Chu-Lagraff et al., "Effect of AIT 082 on Brain NGF mRNA Levels and Transport of AIT-082 Across the Blood-Brain Barrier," Soc. Neurosci. 24: 1941 (1998) (abstract).

P. Di Iorio et al., "The Hypoxanthine Derivative AIT-082 Is Protective Against NMDA- or Kainic Acid-Induced Rat Hippocampal Neurotoxicity in Vivo," Soc. Neurosci. 25: 756 (1999) (abstract).

P. Jimonet et al., "Riluzole Series. Synthesis and in Vivo "Antiglutamate" Activity of 6-Substituted-2-benzothiazolamnes and 3-Substituted 2-imno-benzothiazolines," J. Med. Chem. 42: 2828-2843 (1999).

P.J. Middlemiss et al., "AIT-082, a Unique Purine Derivative, Enhances Nerve Growth Factor Mediated Neurite Outgrowth from PC12 Cells," Neurosci. Lett. 199: 131-134 (1995).

P.J. Middlemiss et al., "The Synthetic Purine AIT-082 Enhances Recovery After Acute Spinal Cord Crush Injury in Rats," Soc. Neurosci. 25: 1002 (1999) (abstract).

P.K. Bridson & T.P. Wierich, "Cycle Homologues of Xanthines, I. Imidaxo[4,5-e][1,4]Diazepine-5,8-Diones," I. Heterocyclic Chem. 25:1179-1182 (1988).

P.R. Birkett et al., "Synthesis and Intramolecular Cyclisation of 5-Aminoimidazolealkanoates and Their Conversion to Purine Derivatives," Synthesis 1991:159 (1991).

PW. Baures et al., "Design, Synthesis, X-Ray Analysis, and Dopamine Receptor-Modulating Activity of Mimics of the 'C5' Hydrogen-Bonded Conformation in the Peptidomimetic 2-Oxo-3-(R)-[(2(S)-Pyrrolidinylcarbonyl)amino]-1-Pyrrolidineacetamide," J. Med. Chem. 37:3677-3683 (1994).

R. Ciccarelli et al., "Guanosine and Related Drugs Stimulate the Production of Neurotrophic Facts from Rat Cultured Astrocytes by Involving Mitogen-Activated Protein Kinase Pathway," Soc. Neurosci. 24: 1013 (1999) (abstract).

R. Huang et al., "Enchancement of Neuronal Cell Excitability by AIT 082 in Rat Hippocampal Neurons and Its Effects on Second Messenger Systems," Soc. Neurosci. 24 1941 (1998) (abstract).

R. Spector, "Hypoxanthine Transport and Metabolism in the Central Nervous System," J. Neurochem. 50: 969-978 (1988).

R. Spector, "Hypoxanthine Transport Through the Blood-Brain Barrier," Neurochem. Res. 12:791-796 (1987).

R.D. Hawkins et al, "Nitric Oxide and Carbon Monoxide as Possible Retrograde Messengers in Hippocampal Long-Term Potentiation," J. Neurobiol. 25:652-665 (1994).

R.E. Callard & A.J.H. Gearing, "The Cytokine Facts Book" (Academic Press, London, 1994), pp. 99-100, 104-105, 191-200, 235-237.

R.E. Dolle & D. McNair, 9-(Sulfoximinoalkyl) Guanine Nucleosides as Potential Antiherpetic Agents,: Tetrahedron Lett. 34:1 (133-136) (1993).

R.G. Blasberg et al., "Transport of $\alpha$-Aminoisobutyric Acid Across Brain Capillary and Celllular Membranes," J. Cereb. Blood Flow Metab. 3: 8-32 (1983).

S. Lehmann et al., "Neurite Outgrowth of Neurons of Rat Dorsal Root Ganglia Induced by New Neurotrophic Substances with Guanidine Group," Neurosci. Lett. 152 57-60 (1993).

S. Van Calenbergh et al., "Synthesis and Structure-Activity Relationship of Analogs of 2'-Deoxy-2'-(3-Methoxybenzamido) adenoisine, a Selective Inhibitor of Trypanosomal Glycosomal Glyceraldehyde-3-Phospate Dehydrogenase," J. Med. Chem. 38:3838-3849 (1995).

S.H. Appel & J.L. McManaman, "Is a Breakdown of the Blood-Brain Barrier Cause or Effect?," Neurobiol. Aging 7:512-514 (1986).

S.H. Snyder, "NO and CO: The Body's Unprecedented Signaling Molecules," 1995 Yearbook of Science and the Future, Engyclopedia Britannica, pp. 84-101.

S.I.Zav'Yalov et al., Synthesis of 4,5,6,7-tetrahydroindole derivates. Chemical Abstracts, 2000, vol. 134, Columbus, Ohio.

S.K. Gupta & R.K. Mishra, "Desensitization of D1 Dopamine Receptors Down-Regulates the Gs$\alpha$ Subunit of G. Protein in SK-N-MC Neuroblastoma Cells," J. Mol. Neurosci. 4:117-123 (1993).

S.K. Gupta & R.K. Mishra, "Up-Regulation of d1 Dopamine Receptors in SK-N-MC Cells After Chrnoic Treatment with SCH 23390," Neurosci, Res. Commun. 15:157-166 (1994).

S.M. MacDonald et al., "Immunological Parameters in the Aged and in Alzheimer's Disease," Clin. Exp. Immunol. 49:123-128 (1982).

U. Diederichsen & H.W. Schmidt, "$\beta$-Homoalanyl-PNA: A Special Case of $\beta$-Peptides with $\beta$-Sheet-Like Backbone Conformation; Organization in Higher Ordered Structures," Eur. J. Org. Chem. 1998:827-835 (1998).

W. Pan et al., "Permeability of the Blood-Brain Barrier to Neurotrophins," Brain Res. 788: 87-94 (1998).

W.A. Banks & A.J. Kastin, "Measurement of Transport of Cytokines Across the Blood-Brain Barrier," Meth. Meurosci, 16:67-77 (1993).

W.A. Banks et al., "Effects of Wheatgerm Agglutinin and Aging on the Regional Brain Uptake of HIV 1 gp120," Life Sci. 65: 81-89 (1999).

W.A. Banks et al., "Measurement of Efflux Rates from Brain to Blood," in Methods in Molecular Biology, Neuropeptide Protocols (G.B. Irvine & C.H. Williams, eds., Humana Press, Totowa, NJ, 1997), pp. 353-360.

W.M. Pardridge, "CNS Drug Design Based on Principles of Blood-Brain Barrier Transport," J. Neurochem. 70: 1781-1792 (1998).

Y. Mizuno et al., "A Novel Protecting Group for the Synthesis of 7$\alpha$-D-Pentofuranosylhypoxanthines," J. Org. Chem. 37:39-42 (1972).

* cited by examiner

EXEMPLARY TETRAHYDROINDOLONE DERIVATIVES AND ANALOGUES
| Example | Compound | MED, IP[a] |
|---|---|---|
| 1<br>Neo 339 | 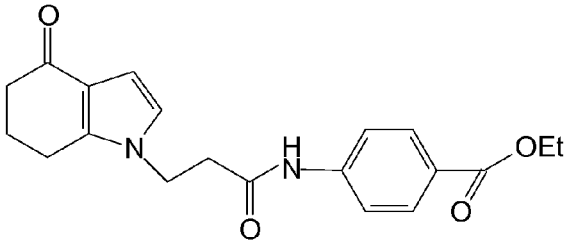 | 0.001 mg/kg |
| 1[c]<br>Neo 362 | 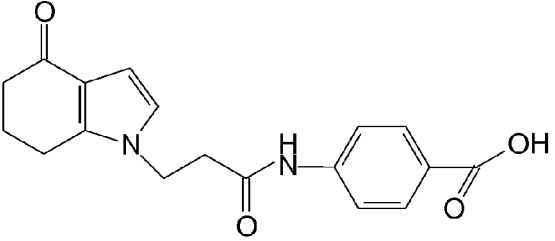 | NT |
[a] Intraperitoneally
[b] Orally
[c] Can be derived from Neo-339 by hydrolysis

METHODS FOR TREATING COGNITIVE/ATTENTION DEFICIT DISORDERS USING TETRAHYDROINDOLONE ANALOGUES AND DERIVATIVES

RELATED APPLICATIONS

This application is a continuation application and claims priority under 35 U.S.C. §120 to U.S. patent application Ser. No. 12/414,539, filed Mar. 30, 2009, a continuation application that claims priority to U.S. patent application Ser. No. 11/002,329, filed Dec. 1, 2004, now U.S. Pat. No. 7,531,670, a continuation application that claims priority to U.S. patent application Ser. No. 10/193,550, filed Jul. 9, 2003, now U.S. Pat. No. 6,982,269, a continuation-in-part application that claims priority to U.S. patent application Ser. No. 09/839,289, filed Apr. 20, 2001, now U.S. Pat. No. 6,759,427, each of which is hereby incorporated by reference in its entirety.

BACKGROUND OF THE INVENTION

1. Field of the Invention

The present invention is directed at methods for treating cognitive/attention deficit disorders in general using tetrahydroindolone derivatives and analogues, particularly tetrahydroindolone derivatives or analogues in which the tetrahydroindolone derivative or analogue is covalently linked to another moiety to form a bifunctional conjugate. More specifically, the present invention is directed at methods and compositions for treating attention deficit disorder and attention deficit hyperactivity disorders in adults and children as well as mild cognitive impairment and dementia.

2. General Background and State of the Art:

Cognitive/attention deficit disorders adversely affect life quality and productivity for millions of persons worldwide. Cognitive/attention deficit disorders such as attention deficit disorder (ADD), attention deficit-hyperactivity disorder (ADHD), mild cognitive impairment and dementia affect both children and adults. In many cases the organic cause remains unknown and presumed inherited. In others, cognitive/attention deficit disorders can be inducing by trauma, disease or aging. Moreover, in many persons mild cognitive impairment may not rise to a clinically identifiable level consequently, these individuals are never labeled ADD or ADHD. However, mild cognitive impairment often results in an inability to concentrate and perform basic tasks associated with normal productive lives.

Cognitive/attention deficit disorders are not only devastating to the afflicted individuals and their family, but society as a whole suffers. Our cultures and economies are deprived the productive contributions that afflicted persons would ordinarily make. Moreover, in many cases society must bear the costs of hospitalizing, incarcerating and/or institutionalizing victims of cognitive/attention deficit disorders.

These disorders are also extremely difficult to treat effectively because of the multiplicity of the symptoms and etiologies. Although many alternative and combination drug therapies have been attempted and proposed, an effective treatment remains elusive. The most common medications used to treat ADD and/or ADHD are stimulants medications, anti-depressant medications, and even anti-convulsant medications. Stimulant medications include Ritalin® (methylphenidate), Dexedrine® (dextroamphetamine), Adderall®, and Cylert® (sodium pemoline). However, these medications, while effective in many persons, are not without side effects.

Ritalin® is the most commonly used stimulant; however, adverse side effects are frequent and include nervousness, insomnia anorexia, and cardiovascular changes. Furthermore, Ritalin® is counter indicated in patients exhibiting anxiety, tension, and agitation. All symptoms commonly associated with ADD and ADHD.

Recently, the diet control medication Obetrol® has been used for treating ADD and ADHD. Obetrol® has been renamed Adderall® and is Dexedrine®/amphetamine composite medication. Adderall® is considered to be less harsh than Ritalin® but is still associated with many adverse side effects including nervousness, insomnia, loss of appetite, addiction, high blood pressure, rapid pulse rate, feelings of suspicion and paranoia. Cylert® is another commonly used central nervous system stimulant. Cylert® (permoline) is an oxazolidine compound known to cause hepatic impairment in many patients. In fact, Canada has recently decertified Cylert® because of the high rate of liver damage associated with its use. Moreover, Cylert® has proven to be ineffective in many patients.

Unfortunately, the many severe side effects associated with conventional ADD and ADHD therapies has caused patent to seek unproven alternative therapies. These include biofeedback, restricted diets, allergy treatments, medicines to correct problems in the inner ear, megavitamins, chiropractic adjustment and bone re-alignment, treatment for yeast infection, eye training and special colored glasses. While most of these alternative therapies do no harm, they can be costly and generally do not provide sustained relief from ADD and ADHD symptoms. Therefore, there remains a need for clinically proven pharmaceutical compositions that palliate the symptoms associated with ADD and ADHD without side effects commonly associated with conventional simulate-based therapies.

INVENTION SUMMARY

One aspect of the present invention includes methods for treating and palliating cognitive/attention deficit disorders in mammals using bifunctional conjugates. In general, a bifunctional conjugate according to the present invention has the schematic structure:

where:
(1) A is a 9-atom bicyclic moiety in which the five-membered ring has 1 to 3 nitrogen atoms, the bicyclic moiety having the structure:

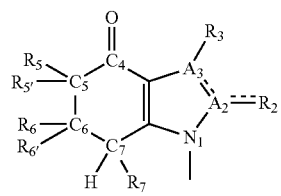

where:
(a) $N_1$ is bonded to L;
(b) $A_2$ and $A_3$ are C or N:

(i) if $A_2$ and $A_3$ are both C and the bond between $A_2$ and $A_3$ is a single bond, then the bond between $A_2$ and $R_2$ is two single bonds to two hydrogen atoms or is a double bond in which $R_2$ is O or S and $R_3$ is two hydrogen atoms;

(ii) if $A_2$ and $A_3$ are both C and the bond between $A_2$ and $A_3$ is a double bond, then $R_3$ is hydrogen, the bond between $A_2$ and $R_2$ is a single bond and $R_2$ is hydrogen, halo, alkyl, alkenyl, aryl, aralkyl, aralkenyl, heteroaryl, heteroaralkyl, or heteroaralkenyl;

(iii) if $A_2$ and $A_3$ are both N, then the bond between $A_2$ and $A_3$ is a double bond and $R_2$ and $R_3$ are not present;

(iv) if $A_2$ is N and $A_3$ is C, then the bond between $A_2$ and $A_3$ is a double bond, $R_2$ is not present, and $R_3$ is hydrogen;

(v) if $A_2$ is C, $A_3$ is N, and the bond between $A_2$ and $A_3$ is a double bond, then $R_3$ is not present, the bond between $A_2$ and $R_2$ is a single bond, and $R_2$ is hydrogen, halo, alkyl, alkenyl, aryl, aralkyl, aralkenyl, heteroaryl, heteroaralkyl, or heteroaralkenyl;

(vi) if $A_2$ is C, $A_3$ is N, and the bond between $A_2$ and $A_3$ is a single bond, then $R_3$ is hydrogen, alkyl, aryl, aralkyl, heteroaryl, or heteroaralkyl, the bond between $A_2$ and $R_2$ is a double bond, and $A_2$ is O or S;

(c) $R_5$ is hydrogen, alkyl, aryl, aralkyl, heteroaryl, heteroaralkyl, alkanoyl, aroyl, heteroaroyl, aralkanoyl, heteroaralkanoyl, $NH_2$, $NHQ_1$, $NQ_1Q_2$, OH, $OQ_1$, or $SQ_1$, where $Q_1$ and $Q_2$ are alkyl, aralkyl, heteroaralkyl, aryl, heteroaryl, alkanoyl, aroyl, aralkanoyl, heteroaralkanoyl, heteroaroyl, alkylsulfonyl, arylsulfonyl, heteroarylsulfonyl, aralkylsulfonyl, or heteroaralkylsulfonyl in which the alkyl portions can be cyclic and can contain from 1 to 3 heteroatoms which can be N, O, or S, and when $Q_1$ and $Q_2$ are present together and are alkyl, they can be taken together to form a 5 or 6 member ring which may contain 1 other heteroatom which can be N, O, or S, of which the N may be further substituted with $Y_2$, where $Y_2$ is alkyl, aryl, heteroaryl, aralkyl, heteroaralkyl, alkanoyl, aroyl, heteroaroyl, aralkanoyl, heteroaralkanoyl, alkylsulfonyl, arylsulfonyl, heteroarylsulfonyl, aralkylsulfonyl, heteroaralkylsulfonyl, alkoxycarbonyl, aryloxycarbonyl, heteroaryloxycarbonyl, aralkoxycarbonyl, heteroaralkoxycarbonyl, alkylaminocarbonyl, arylaminocarbonyl, heteroarylaminocarbonyl, aralkylaminocarbonyl, or heteroaralkylaminocarbonyl, in which the alkyl portions can be cyclic and can contain from 1 to 3 heteroatoms which can be N, O, or S;

(d) $R_{5'}$ is hydrogen unless $R_5$ is alkyl, in which case $R_{5'}$ is hydrogen or the same alkyl as $R_5$;

(e) $R_5$ and $R_{5'}$ can be taken together as a double bond to $C_5$ and can be O, S, $NQ_3$, or C which can be substituted with one or two groups $R_5$, where $Q_3$ is alkyl, aralkyl, heteroaralkyl, aryl, heteroaryl, alkanoyl, aroyl, aralkanoyl, heteroaralkanoyl, or heteroaroyl in which the alkyl portions can be cyclic and can contain from 1 to 3 heteroatoms which can be N, O, or S;

(f) $R_6$ is hydrogen, alkyl, aryl, aralkyl, heteroaryl, heteroaralkyl, $NH_2$, $NHQ_4$, $NQ_4Q_5$, OH, $OQ_4$, or $SQ_4$, where $Q_4$ and $Q_5$ are alkyl, aralkyl, heteroaralkyl, aryl, heteroaryl, alkanoyl, aroyl, aralkanoyl, heteroaralkanoyl, heteroaroyl, alkylsulfonyl, arylsulfonyl, heteroarylsulfonyl, aralkylsulfonyl, or heteroaralkylsulfonyl in which the alkyl portions can be cyclic and can contain from 1 to 3 heteroatoms which can be N, O, or S, and when $Q_1$ and $Q_2$ are present together and are alkyl, they can be taken together to form a 5 or 6 member ring which may contain 1 other heteroatom which can be N, O, or S, of which the N may be further substituted with $Y_2$, where $Y_2$ is alkyl, aryl, heteroaryl, aralkyl, heteroaralkyl, alkanoyl, aroyl, heteroaroyl, aralkanoyl, heteroaralkanoyl, alkylsulfonyl, arylsulfonyl, heteroarylsulfonyl, aralkylsulfonyl, heteroaralkylsulfonyl, alkoxycarbonyl, aryloxycarbonyl, heteroaryloxycarbonyl, aralkoxycarbonyl, heteroaralkoxycarbonyl, alkylaminocarbonyl, arylaminocarbonyl, heteroarylaminocarbonyl, aralkylaminocarbonyl, or heteroaralkylaminocarbonyl, in which the alkyl portions can be cyclic and can contain from 1 to 3 heteroatoms which can be N, O, or S;

(g) $R_{6'}$ is hydrogen unless $R_6$ is alkyl, in which case $R_{6'}$ is hydrogen or the same alkyl as $R_6$;

(h) $R_6$ and $R_{6'}$ can be taken together as a double bond to $C_5$ and can be O, S, $NQ_6$, or C which can be substituted with one or two groups $R_5$, and where Q6 is alkyl, aralkyl, heteroaralkyl, aryl, heteroaryl, alkanoyl, aroyl, aralkanoyl, heteroaralkanoyl, heteroaroyl, alkylsulfonyl, arylsulfonyl, heteroarylsulfonyl, aralkylsulfonyl, or heteroaralkylsulfonyl in which the alkyl portions can be cyclic and can contain from 1 to 3 heteroatoms which can be N, O, or S;

(i) $R_7$ is hydrogen unless $R_5$ is alkyl and $R_{5'}$ is hydrogen, in which case $R_7$ is the same alkyl as $R_5$;

(2) L is a hydrocarbyl moiety of 1 to 6 carbon atoms that can be cyclic, with the hydrocarbyl moiety being optionally substituted with one or more substituents selected from the group consisting of lower alkyl, amino, hydroxy, lower alkoxy, lower alkylamino, lower alkylthio, and oxo; and (3) B is —OZ or $N(Y_1)$-D, where Z is hydrogen, alkyl, aryl, heteroaryl, cycloalkyl, aralkyl, or heteroaralkyl, D is a moiety that promotes absorption of the derivative or analogue, and $Y_1$ is hydrogen, alkyl, aryl, heteroaryl, aralkyl, or heteroaralkyl, which, when taken with D, can form a cyclic 5- or 6-membered saturated structure which can contain one other heteroatom which can be O, N, or S, of which N can be further substituted with $Y_2$, where $Y_2$ is alkyl, aryl, heteroaryl, aralkyl, heteroaralkyl, alkanoyl, aroyl, heteroaroyl, aralkanoyl, heteroaralkanoyl, alkylsulfonyl, arylsulfonyl, heteroarylsulfonyl, aralkylsulfonyl, heteroaralkylsulfonyl, alkoxycarbonyl, aryloxycarbonyl, heteroaryloxycarbonyl, aralkoxycarbonyl, heteroaralkoxycarbonyl, alkylaminocarbonyl, arylaminocarbonyl, heteroarylaminocarbonyl, aralkylaminocarbonyl, or heteroaralkylaminocarbonyl, in which the alkyl portions can be cyclic and can contain from 1 to 3 heteroatoms which can be N, O, or S.

B is either: (i) a moiety with the structure —OZ, where Z is hydrogen, alkyl, aryl, heteroaryl, cycloalkyl, aralkyl, or heteroaralkyl; or (ii) a moiety with the structure —$N(Y_1)$-D, where D is a moiety that promotes absorption of the derivative or analogue that can be substituted as indicated above.

If B is a moiety with the structure —OZ, it is a carboxylic acid or a carboxylic acid ester. Typically, if B is a carboxylic acid ester, the moiety Z is one of methyl, ethyl, propyl, butyl, or isobutyl. More typically, Z is hydrogen or ethyl.

If B is a moiety with the structure —$N(Y_1)$-D, $Y_1$ is hydrogen, alkyl, aryl, heteroaryl, aralkyl, or heteroaralkyl, which, when taken with D, can form a cyclic 5- or 6-membered saturated ring which can contain one other heteroatom which can be O, N, or S, of which N can be further substituted with $Y_2$, where $Y_2$ is alkyl, aryl, heteroaryl, aralkyl, heteroaralkyl, alkanoyl, aroyl, heteroaroyl, aralkanoyl, heteroaralkanoyl, alkylsulfonyl, arylsulfonyl, heteroarylsulfonyl, aralkylsulfonyl, heteroaralkylsulfonyl, alkoxycarbonyl, aryloxycarbonyl, heteroaryloxycarbonyl, aralkoxycarbonyl, heteroaralkoxycarbonyl, alkylaminocarbonyl, arylaminocarbonyl, heteroarylaminocarbonyl, aralkylaminocarbonyl, heteroaralkylaminocarbonyl, in which the alkyl portions can be cyclic and can contain from 1 to 3 heteroatoms which can be N, O, or S. Typically, $Y_1$ is hydrogen or lower alkyl. Most typically, $Y_1$ is hydrogen.

Typically, the tetrahydroinolone derivative or analogue has a logP of from about 1 to about 4 to enhance bioavailability and central nervous system (CNS) penetration. Using this guideline, one of ordinary skill in the art can choose the appropriate moieties B for a particular moiety A in order to ensure the bioavailability and CNS penetration of a tetrahydroinolone analogue or derivative according to the present invention. For example, if a highly hydrophobic moiety A is chosen, with particularly hydrophobic substituents on the tetrahydroinolone moiety, then a more hydrophilic moiety B can be used.

Typically, A is a tetrahydroindolone moiety.

In one alternative, B is a moiety containing at least one carboxyl, carboxamide, carboxyl ester, or carbonyl function.

In another alternative, B is a cyclic or acyclic moiety containing at least one hydroxyl, primary amino, secondary amino, tertiary amino, sulfhydryl, or sulfonamidyl function.

Particular examples of bifunctional conjugates according to the present invention include: (1) 4-[3-(4-oxo-4,5,6,7-tetrahydroindolon-1-yl)propionylamino} benzoic acid ethyl ester; and 4-[3-(4-oxo-4,5,6,7-tetrahydroindolon-1-yl)propionylamino} benzoic acid.

In one aspect of the present invention tetrahydroindolone derivatives and analogues described above treat and/or palliate attention deficit disorder (ADH), attention deficit hyperactivity disorder (ADHD), mild cognitive impairment, and dementia, whether due to inherited factors, disease, injury or aging. The present inventors believe, without being limited to this theory, that improvement in cognition and attention may be achieved by stimulating neuronal function involving neuronal regeneration or axo-dendritic complexity in the central and peripheral nervous systems comprising.

The method of treating and/or palliating cognition/attention deficit disorders includes the step of administering an effective amount of a tetrahydroinolone derivative or analogue according to the present invention to the mammal. One method for treating cognition/attention deficit disorders using the tetrahydroinolone derivatives and analogues according to the present invention is a method of stimulating neuronal function such as improved cognition, involving by initiating neurogenesis in the central nervous system of a mammal comprising the step of administering an effective amount of a tetrahydroinolone derivative or analogue according to the present invention to the mammal. Yet another aspect of a method of use of tetrahydroinolone derivatives and analogues according to the present invention is a method of stimulating neuronal function involving mechanism associated with neuroprotection in the central or peripheral nervous system of a mammal comprising the step of administering an effective amount of a tetrahydroindolone derivative or analogue according to the present invention to the mammal.

Another aspect of the present invention is pharmaceutical compositions. A pharmaceutical composition according to the present invention comprises: (1) an effective amount of a tetrahydroindolone derivative or analogue according to the present invention; and (2) a pharmaceutically acceptable carrier.

BRIEF DESCRIPTION OF THE DRAWINGS

The following invention will become better understood with reference to the specification, appended claims, and accompanying drawings where:

FIG. 1 is a table depicting a number of the tetrahydroindolone derivatives or analogues according to the present invention together with the minimum effective dose in the passive avoidance test for neurological activity in mice with intraperitoneal administration.

DETAILED DESCRIPTION OF THE PREFERRED EMBODIMENTS

I. Tetrahydroindolone Derivatives and Analogues

One aspect of the present invention is a method of treating cognitive/attention deficit disorders in general using tetrahydroindolone derivatives and analogues. For the purposes of the present invention, and not intended as a limitation, the term "cognitive/attention deficit disorders" shall include Attention Deficit Disorder (ADD), Attention Deficit Hyperactivity Disorder (ADHD), mild cognitive impairment, and dementia. These cognitive/attention deficit disorders may result from inherited factors, disease, injury or other, presently unknown physiological, anatomical, metabolic, environmental, or social factors. Moreover, the methods and compositions of the present invention are also useful as neuroprotectants.

In its most general aspect, the method of the present invention include administering to a mammal an effective amount of a bifunctional conjugate according to the present invention has the schematic structure:

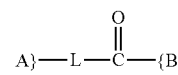

where:
(1) A is a 9-atom bicyclic moiety in which the five-membered ring has 1 to 3 nitrogen atoms, the bicyclic moiety having the structure:

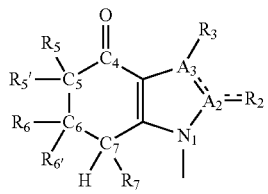

where:
(a) $N_1$ is bonded to L;
(b) $A_2$ and $A_3$ are C or N:
(i) if $A_2$ and $A_3$ are both C and the bond between $A_2$ and $A_3$ is a single bond, then the bond between $A_2$ and $R_2$ is two single bonds to two hydrogen atoms or is a double bond in which $R_2$ is O or S and $R_3$ is two hydrogen atoms;
(ii) if $A_2$ and $A_3$ are both C and the bond between $A_2$ and $A_3$ is a double bond, then $R_3$ is hydrogen, the bond between $A_2$ and $R_2$ is a single bond and $R_2$ is hydrogen, halo, alkyl, alkenyl, aryl, aralkyl, aralkenyl, heteroaryl, heteroaralkyl, or heteroaralkenyl;
(iii) if $A_2$ and $A_3$ are both N, then the bond between $A_2$ and $A_3$ is a double bond and $R_2$ and $R_3$ are not present;
(iv) if $A_2$ is N and $A_3$ is C, then the bond between $A_2$ and $A_3$ is a double bond, $R_2$ is not present, and $R_3$ is hydrogen;

(v) if $A_2$ is C, $A_3$ is N, and the bond between $A_2$ and $A_3$ is a double bond, then $R_3$ is not present, the bond between $A_2$ and $R_2$ is a single bond, and $R_2$ is hydrogen, halo, alkyl, alkenyl, aryl, aralkyl, aralkenyl, heteroaryl, heteroaralkyl, or heteroaralkenyl;

(vi) if $A_2$ is C, $A_3$ is N, and the bond between $A_2$ and $A_3$ is a single bond, then $R_3$ is hydrogen, alkyl, aryl, aralkyl, heteroaryl, or heteroalkyl, the bond between $A_2$ and $R_2$ is a double bond, and $A_2$ is O or S;

(c) $R_5$ is hydrogen, alkyl, aryl, aralkyl, heteroaryl, heteroaralkyl, alkanoyl, aroyl, heteroaroyl, aralkanoyl, heteroaralkanoyl, $NH_2$, $NHQ_1$, $NQ_1Q_2$, OH, $OQ_1$, or $SQ_1$, where $Q_1$ and $Q_2$ are alkyl, aralkyl, heteroaralkyl, aryl, heteroaryl, alkanoyl, aroyl, aralkanoyl, heteroaralkanoyl, heteroaroyl, alkylsulfonyl, arylsulfonyl, heteroarylsulfonyl, aralkylsulfonyl, or heteroaralkylsulfonyl in which the alkyl portions can be cyclic and can contain from 1 to 3 heteroatoms which can be N, O, or S, and when $Q_1$ and $Q_2$ are present together and are alkyl, they can be taken together to form a 5 or 6 member ring which may contain 1 other heteroatom which can be N, O, or S, of which the N may be further substituted with $Y_2$, where $Y_2$ is alkyl, aryl, heteroaryl, aralkyl, heteroaralkyl, alkanoyl, aroyl, heteroaroyl, aralkanoyl, heteroaralkanoyl, alkylsulfonyl, arylsulfonyl, heteroarylsulfonyl, aralkylsulfonyl, heteroaralkylsulfonyl, alkoxycarbonyl, aryloxycarbonyl, heteroaryloxycarbonyl, aralkoxycarbonyl, heteroaralkoxycarbonyl, alkylaminocarbonyl, arylaminocarbonyl, heteroarylaminocarbonyl, aralkylaminocarbonyl, or heteroaralkylaminocarbonyl, in which the alkyl portions can be cyclic and can contain from 1 to 3 heteroatoms which can be N, O, or S;

(d) $R_{5'}$ is hydrogen unless $R_5$ is alkyl, in which case $R_{5'}$ is hydrogen or the same alkyl as $R_5$;

(e) $R_5$ and $R_{5'}$ can be taken together as a double bond to $C_5$ and can be O, S, $NQ_3$, or C which can be substituted with one or two groups $R_5$, where $Q_3$ is alkyl, aralkyl, heteroaralkyl, aryl, heteroaryl, alkanoyl, aroyl, aralkanoyl, heteroaralkanoyl, or heteroaroyl in which the alkyl portions can be cyclic and can contain from 1 to 3 heteroatoms which can be N, O, or S;

(f) $R_6$ is hydrogen, alkyl, aryl, aralkyl, heteroaryl, heteroaralkyl, $NH_2$, $NHQ_4$, $NQ_4Q_5$, OH, $OQ_4$, or $SQ_4$, where $Q_4$ and $Q_5$ are alkyl, aralkyl, heteroaralkyl, aryl, heteroaryl, alkanoyl, aroyl, aralkanoyl, heteroaralkanoyl, heteroaroyl, alkylsulfonyl, arylsulfonyl, heteroarylsulfonyl, aralkylsulfonyl, or heteroaralkylsulfonyl in which the alkyl portions can be cyclic and can contain from 1 to 3 heteroatoms which can be N, O, or S, and when $Q_1$ and $Q_2$ are present together and are alkyl, they can be taken together to form a 5 or 6 member ring which may contain 1 other heteroatom which can be N, O, or S, of which the N may be further substituted with $Y_2$, where $Y_2$ is alkyl, aryl, heteroaryl, aralkyl, heteroaralkyl, alkanoyl, aroyl, heteroaroyl, aralkanoyl, heteroaralkanoyl, alkylsulfonyl, arylsulfonyl, heteroarylsulfonyl, aralkylsulfonyl, heteroaralkylsulfonyl, alkoxycarbonyl, aryloxycarbonyl, heteroaryloxycarbonyl, aralkoxycarbonyl, heteroaralkoxycarbonyl, alkylaminocarbonyl, arylaminocarbonyl, heteroarylaminocarbonyl, aralkylaminocarbonyl, or heteroaralkylaminocarbonyl, in which the alkyl portions can be cyclic and can contain from 1 to 3 heteroatoms which can be N, O, or S;

(g) $R_{6'}$ is hydrogen unless $R_6$ is alkyl, in which case $R_{6'}$ is hydrogen or the same alkyl as $R_6$;

(h) $R_6$ and $R_{6'}$ can be taken together as a double bond to $C_5$ and can be O, S, $NQ_6$, or C which can be substituted with one or two groups $R_5$, and where Q6 is alkyl, aralkyl, heteroaralkyl, aryl, heteroaryl, alkanoyl, aroyl, aralkanoyl, heteroaralkanoyl, heteroaroyl, alkylsulfonyl, arylsulfonyl, heteroarylsulfonyl, aralkylsulfonyl, or heteroaralkylsulfonyl in which the alkyl portions can be cyclic and can contain from 1 to 3 heteroatoms which can be N, O, or S;

(i) $R_7$ is hydrogen unless $R_5$ is alkyl and $R_{5'}$ is hydrogen, in which case $R_7$ is the same alkyl as $R_5$;

(2) L is a hydrocarbyl moiety of 1 to 6 carbon atoms that can be cyclic, with the hydrocarbyl moiety being optionally substituted with one or more substituents selected from the group consisting of lower alkyl, amino, hydroxy, lower alkoxy, lower alkylamino, lower alkylthio, and oxo; and (3) B is —OZ or N($Y_1$)-D, where Z is hydrogen, alkyl, aryl, heteroaryl, cycloalkyl, aralkyl, or heteroaralkyl, D is a moiety that promotes absorption of the derivative or analogue, and $Y_1$ is hydrogen, alkyl, aryl, heteroaryl, aralkyl, or heteroaralkyl, which, when taken with D, can form a cyclic 5- or 6-membered saturated structure which can contain one other heteroatom which can be O, N, or S, of which N can be further substituted with $Y_2$, where $Y_2$ is alkyl, aryl, heteroaryl, aralkyl, heteroaralkyl, alkanoyl, aroyl, heteroaroyl, aralkanoyl, heteroaralkanoyl, alkylsulfonyl, arylsulfonyl, heteroarylsulfonyl, aralkylsulfonyl, heteroaralkylsulfonyl, alkoxycarbonyl, aryloxycarbonyl, heteroaryloxycarbonyl, aralkoxycarbonyl, heteroaralkoxycarbonyl, alkylaminocarbonyl, arylaminocarbonyl, heteroarylaminocarbonyl, aralkylaminocarbonyl, or heteroaralkylaminocarbonyl, in which the alkyl portions can be cyclic and can contain from 1 to 3 heteroatoms which can be N, O, or S.

As shown in Formula (I), the moiety A has a six-membered ring fused to a five-membered ring, as in a tetrahydroindolone moiety. The five-membered ring can have one, two, or three nitrogen atoms as indicated, but always has a nitrogen atom at the position that would correspond to the 9-position of a purine moiety with which the tetrahydroindolone moiety is isosteric. Typically, the five-membered ring has one nitrogen atom as in tetrahydroindolone. This nitrogen atom is covalently bonded to the linker L.

Typically A is a tetrahydroindolone moiety in which $A_7$ is carbon and $A_8$ is carbon. The tetrahydroindolone moiety can be variously substituted.

Typically, $Y_1$ is hydrogen or lower alkyl. Most typically, $Y_1$ is hydrogen.

In many examples, in a tetrahydroindolone analogue or derivative according to the present invention, the moiety B has a biological, physiological, or pharmacological function, and the tetrahydroindolone analogue or derivative is referred to as a "bifunctional conjugate." However, it is not required in tetrahydroindolone analogues or derivatives according to the present invention that the moiety B have a biological, physiological, or pharmacological function. The moiety B can serve as a carrier to improve bioavailability or to optimize the physical characteristics of the molecule without having a separate biological, physiological function, or pharmacological function.

In many tetrahydroindolone analogues or derivatives according to the present invention, the moiety B includes a p-aminobenzoic acid, or a p-aminobenzoic acid ester. However, the moiety B can include other groups.

Typically, the tetrahydroindolone derivative or analogue has a logP of from about 1 to about 4 to enhance bioavailability and central nervous system (CNS) penetration. Using this guideline, one of ordinary skill in the art can choose the appropriate moieties B for a particular moiety A in order to ensure the bioavailability and CNS penetration of a tetrahydroindolone analogue or derivative according to the present invention. For example, if a highly hydrophobic moiety A is chosen, with particularly hydrophobic substituents on the tetrahydroindolone moiety, then a more hydrophilic moiety B can be used.

The linker L is described further below. L is a hydrocarbyl moiety of 1 to 6 carbon atoms that can be cyclic, with the hydrocarbyl moiety being optionally substituted with one or more substituents selected from the group consisting of lower alkyl, amino, hydroxy, lower alkoxy, lower alkylamino, lower alkylthio, and oxo.

In accordance with the present invention, and as used herein, the following terms, when appearing alone or as part of a moiety including other atoms or groups, are defined with the following meanings, unless explicitly stated otherwise. In addition, all groups described herein can be optionally substituted unless such substitution is excluded. The term "alkyl," as used herein at all occurrences, refers to saturated aliphatic groups including straight-chain, branched-chain, and cyclic groups, all of which can be optionally substituted. Preferred alkyl groups contain 1 to 10 carbon atoms. Suitable alkyl groups include methyl, ethyl, and the like, and can be optionally substituted. The term "alkenyl," as used herein at all occurrences, refers to unsaturated groups which contain at least one carbon-carbon double bond and includes straight-chain, branched-chain, and cyclic groups, all of which can be optionally substituted. Preferable alkenyl groups have 2 to 10 carbon atoms. The term "alkoxy" refers to the ether —O-alkyl, where alkyl is defined as above. The term "aryl" refers to aromatic groups which have at least one ring having a conjugated π-electron system and includes carbocyclic aryl and biaryl, both of which may be optionally substituted. Preferred aryl groups have 6 to 10 carbon atoms. The term "aralkyl" refers to an alkyl group substituted with an aryl group. Suitable aralkyl groups include benzyl and the like; these groups can be optionally substituted. The term "aralkenyl" refers to an alkenyl group substituted with an aryl group. The term "heteroaryl" refers to carbon-containing 5-14 membered cyclic unsaturated radicals containing one, two, three, or four O, N, or S heteroatoms and having 6, 10, or 14 π-electrons delocalized in one or more rings, e.g., pyridine, oxazole, indole, thiazole, isoxazole, pyrazole, pyrrole, each of which can be optionally substituted as discussed above. The term "sulfonyl" refers to the group —S(O$_2$)—. The term "alkanoyl" refers to the group —C(O)Rg, where Rg is alkyl. The term "aroyl" refers to the group —C(O)Rg, where Rg is aryl. Similar compound radicals involving a carbonyl group and other groups are defined by analogy. The term "aminocarbonyl" refers to the group —NHC(O)—. The term "oxycarbonyl" refers to the group —OC(O)—. The term "heteroaralkyl" refers to an alkyl group substituted with a heteroaryl group. Similarly, the term "heteroaralkenyl" refers to an alkenyl group substituted with a heteroaryl group. Where used herein, the term "lower," in reference to an alkyl or the alkyl portion of an another group including alkyl, is defined as a group containing one to ten carbon atoms, more typically one to six carbon atoms. The term "optionally substituted" refers to one or more substituents that are typically lower alkyl, aryl, amino, hydroxy, lower alkoxy, aryloxy, lower alkylamino, arylamino, lower alkylthio, arylthio, or oxo, in some cases, other groups can be included, such as cyano, acetoxy, or halo. The term "halo" refers generally to fluoro, chloro, bromo, or iodo; more typically, "halo" refers to chloro.

A preferred linker has the structure —(CH$_2$)$_n$— wherein n is an integer from 1 to 6. As detailed below, for most preferred embodiments of tetrahydroindolone derivatives and analogues according to the present invention, a preferred linker has n equal to 2 or 3. The following are particular examples of tetrahydroindolone derivatives and analogues according to the present invention.

A number of tetrahydroindolone derivatives or analogues according to the present invention are optically active, owing to the presence of chiral carbons or other centers of asymmetry. In cases where tetrahydroindolone derivatives or analogues according to the present invention are optically active, all of the possible enantiomers or diastereoisomers are included unless otherwise indicated despite possible differences in activity.

Particularly preferred tetrahydroindolone moieties for the moiety A are described below.

One example of a tetrahydroindolone moiety for the moiety A is a tetrahydroindolone moiety of Formula (II), below, in which:

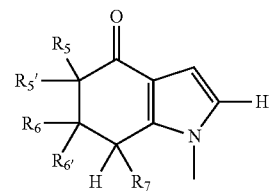

(1) R$_5$ is hydrogen, alkyl, aryl, aralkyl, heteroaryl, heteroaralkyl, alkanoyl, aroyl, heteroaroyl, aralkanoyl, heteroaralkanoyl, NH$_2$, NHW$_1$, NQ$_1$Q$_2$, OH, OQ$_1$, or SQ$_1$, where Q$_1$ and Q$_2$ are alkyl, aralkyl, heteroaralkyl, aryl, heteroaryl, alkanoyl, aroyl, aralkanoyl, heteroaralkanoyl, or heteroaroyl in which the alkyl portions can be cyclic and can contain from 1 to 3 heteroatoms which can be N, O, or S, and where W$_1$ is alkyl, aralkyl, heteroaralkyl, aryl, heteroaryl, alkanoyl, aroyl, aralkanoyl, heteroaralkanoyl, or heteroaroyl, alkylsulfonyl, arylsulfonyl, heteroarylsulfonyl, aralkylsulfonyl, or heteroaralkylsulfonyl in which the alkyl portions can be cyclic and can contain from 1 to 3 heteroatoms which can be N, O, or S;

(2) R$_5'$ is hydrogen;

(3) R$_6$ is hydrogen, alkyl, aryl, aralkyl, heteroaryl, heteroaralkyl, alkanoyl, aroyl, heteroaroyl, aralkanoyl, heteroaralkanoyl, NH$_2$, NHW$_1$, NQ$_1$Q$_2$, OH, OQ$_1$, or SQ$_1$, where Q$_1$ and Q$_2$ are alkyl, aralkyl, heteroaralkyl, aryl, heteroaryl, alkanoyl, aroyl, aralkanoyl, heteroaralkanoyl, or heteroaroyl in which the alkyl portions can be cyclic and can contain from 1 to 3 heteroatoms which can be N, O, or S, and where W$_1$ is alkyl, aralkyl, heteroaralkyl, aryl, heteroaryl, alkanoyl, aroyl, aralkanoyl, heteroaralkanoyl, or heteroaroyl, alkylsulfonyl, arylsulfonyl, heteroarylsulfonyl, aralkylsulfonyl, or heteroaralkylsulfonyl in which the alkyl portions can be cyclic and can contain from 1 to 3 heteroatoms which can be N, O, or S;

(4) R$_6'$ is hydrogen; and (5) R$_7$ is hydrogen.

In one particularly preferred embodiment, R$_5$, R$_5'$, R$_6$, R$_6'$, and R$_7$ are all hydrogen. In this particularly preferred embodiment, the moiety A is an unsubstituted tetrahydroindolone moiety.

In addition to these examples of moieties suitable as moiety A, other moieties can serve as moiety A, including moieties with two or three nitrogen atoms or moieties with substituents at R$_2$.

In general, tetrahydroindolone derivatives and analogues that are within the scope of the present invention also include salts and prodrug esters of these bifunctional conjugates. It is well known that organic compounds, including substituted tetrahydroindolones and other components of these tetrahydroindolone derivatives and analogues, have multiple groups that can accept or donate protons, depending upon the pH of the solution in which they are present. These groups include carboxyl groups, hydroxyl groups, amino groups, sulfonic acid groups, and other groups known to be involved in acid-base reactions. The recitation of a tetrahydroindolone derivative or analogue includes such salt forms as occur at physiological pH or at the pH of a pharmaceutical composition unless specifically excluded.

Similarly, prodrug esters can be formed by reaction of either a carboxyl or a hydroxyl group on the tetrahydroindolone derivative or analogue with either an acid or an alcohol to form an ester. Typically, the acid or alcohol includes a lower alkyl group such as methyl, ethyl, propyl, isopropyl, butyl, isobutyl, and tertiary butyl. These groups can be substituted with substituents such as hydroxy, or other substituents. Such prodrugs are well known in the art and need not be described further here. The prodrug is converted into the active compound by hydrolysis of the ester linkage, typically by intracellular enzymes. Other suitable groups that can be used to form prodrug esters are well known in the art.

As indicated above, the linker L is a hydrocarbyl moiety of one to six carbon atoms, with the hydrocarbyl moiety being optionally substituted with one or more substituents selected from the group consisting of lower alkyl, amino, hydroxy, lower alkoxy, lower alkylamino, lower alkylhio, and oxo. Preferably, the linker L has the structure —$(CH_2)_n$— wherein n is an integer from 1 to 6. As detailed below, for most preferred embodiments of tetrahydroindolone derivatives and analogues according to the present invention, a preferred linker has n equal to 2 or 3.

The moiety B is either: (i) —OZ, where Z is hydrogen, alkyl, aryl, heteroaryl, cycloalkyl, aralkyl, or heteroaralkyl; or (ii) N($Y_1$)-D, where D is a moiety that promotes absorption of the derivative or analogue, and $Y_1$ is hydrogen, alkyl, aryl, heteroaryl, aralkyl, or heteroaralkyl, which, when taken with D, can form a cyclic 5- or 6-membered saturated ring which can contain one other heteroatom which can be O, N, or S, of which N can be further substituted with $Y_2$, where $Y_2$ is alkyl, aryl, heteroaryl, aralkyl, heteroaralkyl, alkanoyl, aroyl, heteroaroyl, aralkanoyl, heteroaralkanoyl, alkylsulfonyl, arylsulfonyl, heteroarylsulfonyl, aralkylsulfonyl, heteroaralkylsulfonyl, alkoxycarbonyl, aryloxycarbonyl, heteroaryloxycarbonyl, aralkoxycarbonyl, heteroaralkoxycarbonyl, alkylaminocarbonyl, arylaminocarbonyl, heteroarylaminocarbonyl, aralkylaminocarbonyl, heteroaralkylaminocarbonyl, in which the alkyl portions can be cyclic and can contain from 1 to 3 heteroatoms which can be N, O, or S. Typically, $Y_1$ is hydrogen. Where the moiety B is —OZ, the moiety B is a carboxylic acid or carboxylic acid or ester. Typically, where B is a carboxylic acid ester, the moiety Z is a lower alkyl, such as methyl, ethyl, butyl, propyl, or isopropyl.

In one alternative, the moiety D, as described above, is a moiety having at least one polar, charged, or hydrogen-bond-forming group to improve the metabolic and bioavailability properties of the tetrahydroindolone derivative or analogue. The moiety D can be, but is not limited to, a moiety with physiological or biological activity such as nootropic activity. In one alternative, the moiety D can be a moiety containing at least one carboxyl, carboxamide, carboxyl ester, or carbonyl function. In another alternative, the moiety D can be a moiety containing at least one hydroxyl, primary amino, secondary amino, tertiary amino, sulfhydryl, or sulfonamidyl function. The moiety D can be cyclic or acyclic. Preferred examples of the moiety D are described below.

When the moiety D is a cyclic or acyclic moiety containing at least one carbonyl, carboxamide, carboxyl ester, or carbonyl function, in one preferred example, D is a carboxylic acid or carboxylic acid ester with the structure

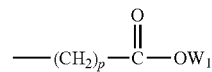

wherein p is an integer from 1 to 6 and $W_1$ is selected from the group consisting of hydrogen and lower alkyl. Typically, if $W_1$ is lower alkyl, it is methyl, ethyl, propyl, butyl, or isobutyl. Typically, p is 3. Typically, $W_1$ is hydrogen or ethyl.

In another preferred example, D and $Y_1$ are taken together to form a piperazine derivative as described in D. Manetti et al., "Molecular Simplification of 1,4-Diazabicyclo[4.3.0] nonan-9-ones Gives piperazine Derivatives That Maintain High Nootropic Activity," *J. Med. Chem.* 43: 4499-4507 ("Manetti et al. (2000) (II)"). B is an analogue of structure

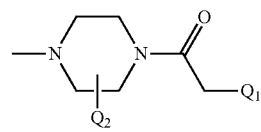

wherein $Q_1$ is hydrogen, methyl, ethyl, butyl, or propyl, $Q_2$ is hydrogen or methyl, where, if $Q_2$ is methyl, it can be located at either of the two possible positions in the piperazine ring.

In another preferred example, D has the structure

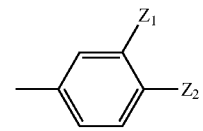

where one of $Z_1$ and $Z_2$ is hydrogen, and the other of $Z_1$ and $Z_2$ is —COOH or —COO$W_1$, wherein $W_1$ is alkyl. Typically, $W_1$ is selected from the group consisting of methyl, ethyl, propyl, butyl, and isobutyl. Either of $Z_1$ or $Z_2$ can be hydrogen. When $Z_1$ is hydrogen and $Z_2$ is —COOH, the moiety B is p-aminobenzoic acid (PABA). When $Z_1$ is —COOH and $Z_2$ is hydrogen, the moiety B is m-aminobenzoic acid (MABA). When $Z_1$ is hydrogen and $Z_2$ is —COO$W_1$, the moiety B is an ester of p-aminobenzoic acid (PABA). When $Z_1$ is —COO$W_1$ and $Z_2$ is hydrogen, the moiety B is an ester of m-aminobenzoic acid (MABA). Typically, these esters are ethyl esters.

When the moiety D is a moiety that contains at least one hydroxyl, primary amino, secondary amino, tertiary amino, sulfhydryl, or sulfonamidyl function, in one preferred example, D is a phenylsulfonamidyl moiety of structure

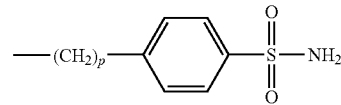

wherein p is an integer from 0 to 6. Typically, p is 2.

In another preferred example, D is an alkylpyridyl moiety of structure

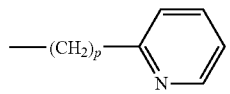

wherein p is an integer from 1 to 6. Typically, p is 1.

In another preferred example, D is a dialkylaminoalkyl moiety of the structure

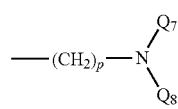

wherein p is an integer from 1 to 6 and $Q_7$ and $Q_8$ are alkyl, aralkyl, heteroaralkyl, aryl, heteroaryl, alkanoyl, aroyl, aralkanoyl, heteroaralkanoyl, or heteroaroyl in which the alkyl portions can be cyclic and can contain from 1 to 3 heteroatoms which can be N, O, or S, and when $Q_7$ and $Q_8$ are present together and are alkyl, they can be taken together to form a 5 or 6 member ring which may contain 1 other heteroatom which can be N, O, or S, of which the N may be further substituted with $Y_2$, where $Y_2$ is alkyl, aryl, heteroaryl, aralkyl, heteroaralkyl, alkanoyl, aroyl, heteroaroyl, aralkanoyl, heteroaralkanoyl, alkylsulfonyl, arylsulfonyl, heteroarylsulfonyl, aralkylsulfonyl, heteroaralkylsulfonyl, alkoxycarbonyl, aryloxycarbonyl, heteroaryloxycarbonyl, aralkoxycarbonyl, heteroaralkoxycarbonyl, alkylaminocarbonyl, arylaminocarbonyl, heteroarylaminocarbonyl, aralkylaminocarbonyl, or heteroaralkylaminocarbonyl, in which the alkyl portions can be cyclic and can contain from 1 to 3 heteroatoms which can be N, O, or S, and where $W_1$ is alkyl, aralkyl, heteroaralkyl, aryl, heteroaryl, alkanoyl, aroyl, aralkanoyl, heteroaralkanoyl, or heteroaroyl, alkylsulfonyl, arylsulfonyl, heteroarylsulfonyl, aralkylsulfonyl, or heteroaralkylsulfonyl in which the alkyl portions can be cyclic and can contain from 1 to 3 heteroatoms which can be N, O, or S. Where $Q_7$ and $Q_8$ can be taken together to form a five or six member optionally substituted ring, the ring is typically pyrrolidine, piperidine, or morpholine. The pyrrolidine ring can be optionally substituted with oxo. The piperidine ring can be optionally substituted with methyl or ethyl. Typically, p is 2 or 3.

In another preferred example, D is an alkylpyrrolidine moiety of the structure

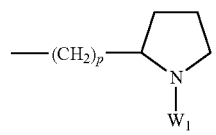

wherein p is an integer from 1 to 6 and $W_1$ is selected from the group consisting of methyl, ethyl, and propyl. Typically, $W_1$ is methyl. Typically, p is 2.

Preferably, a tetrahydroindolone analogue or derivative according to the present invention has a logP of from about 1 to about 4 in order to optimize bioavailability and CNS penetration of the tetrahydroindolone analogue or derivative.

In general, any moiety A can be combined with any linker L and any moiety B, including the appropriate moiety D, to produce a tetrahydroindolone analogue or derivative according to the present invention. However, there exist a number of particularly preferred tetrahydroindolone analogues or derivatives according to the present invention. These include the following:

(1) 4-[3-(4-oxo-4,5,6,7-tetrahydroindolon-1-yl)propionylamino} benzoic acid ethyl ester (Example 1); and (2) 4-[3-(4-oxo-4,5,6,7-tetrahydroindolon-1-yl)propionylamino} benzoic acid.

II. Methods of Synthesis of Tetrahydroindolone Derivatives and Analogues According to the Present Invention Methods for synthesis of tetrahydroindolone derivatives and analogues according to the present invention are modified from those described, for example, in U.S. Pat. No. 5,091,432 to Glasky, incorporated herein by this reference. In one general route in which the tetrahydroindolone derivatives and analogues according to the present invention contain a tetrahydroindolone moiety, the tetrahydroindolone moiety is substituted with a linker which in turn is linked to the moiety B that completes the molecule as described above. This route comprises the steps of: (1) synthesizing an appropriately substituted tetrahydroindolone moiety linked to an aliphatic linker in which the linker is terminated with a carboxyl group protected such as with an alkyl ester; (2) hydrolyzing the alkyl ester (or other analogous protecting group) to yield a carboxylic acid; (3) activating the free carboxylic acid by converting it to a nitrophenyl ester; (4) reacting the nitrophenyl ester with an appropriate group that can form an amide or other stable covalent linkage with the carboxyl moiety, with appropriate protection for the moiety reacting with the ester if required; and (5) hydrolyzing the protective group protecting the moiety reacting with the ester to produce the final product.

The length of the aliphatic linker covalently bound to the tetrahydroindolone moiety can be varied to vary the distance between the tetrahydroindolone moiety and the moiety B in the tetrahydroindolone derivative or analogue.

Other methods for functionalization of the tetrahydroindolone moiety include the use of Michael addition of the 1-nitrogen of the tetrahydroindolone moiety to the terminal methylene of an acrylamide which already contains the moiety B. (see below)

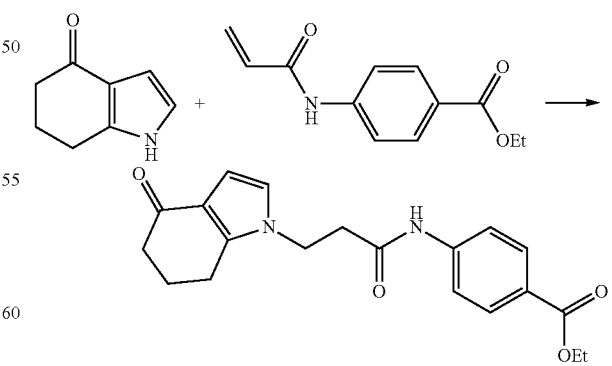

Another reaction that may be used to functionalize tetrahydroindolones is the Mitsunobu reaction. The Mitsunobu reaction is a highly versatile method for the introduction of widely varying functionality upon the tetrahydroindolone moiety, because of the wide assortment of primary alcohols that are commercially available for use in this reaction.

Yet another method of synthesis of tetrahydroindolone derivatives or analogues is via an appropriately substituted tetrahydrobenzofuranone. The tetrahydro bezofuranone is reacted with a primary amine attached to the appropriate linker and B moiety (see below). Matsumoto, et al. "A Facile Synthesis of 4-Oxo-4,5,6,7-tetrahydroindolone." Heterocycles 22: 2313-2316 (1984)

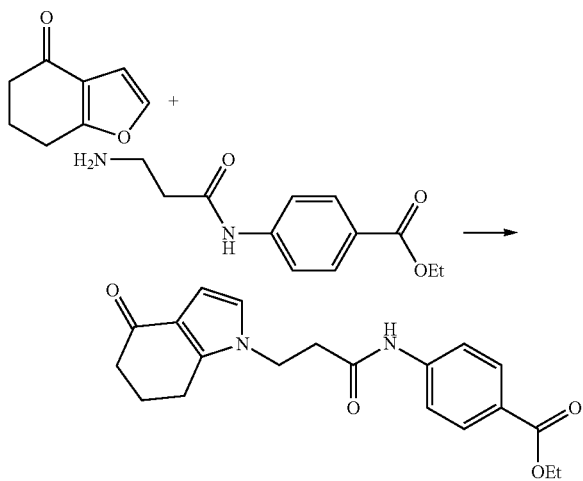

Synthesis of 4-[3-(4-Oxo-4,5,6,7-tetrahydroindolon-1-yl)propionylamino} Benzoic Acid Ethyl Ester To a solution of acryloyl chloride (1.08 mL, 13.32 mmol) in dry dichloromethane (10 mL) was slowly added dropwise, via addition funnel, a solution of 4-aminobenzoic acid ethyl ester (2.0 g, 12.11 mmol) and triethylamine (1.86 mL, 13.32 mmol) in dry dichloromethane (5 mL) over about 30 minutes. The reaction was stirred at room temperature for 16 hours. The solution was then partitioned between dichloromethane and water in a separatory funnel. The organic layer was washed with 2 N HCl, dried with sodium sulfate, and concentrated in vacuo to dryness. The resulting residue was triturated with hexane, and vacuum filtered to yield 2.02 g (76%) of 4-acryloylaminobenzoic acid ethyl ester as a solid.

In the second step, 4-acryloylaminobenzoic acid ethyl ester (200 mg, 0.91 mmol), 1,5,6,7-tetrahydro-4H-indol-4-one (123 mg, 0.91 mmol) and potassium carbonate (126 mg, 0.91 mmol) were combined in dry N,N-dimethylformamide (3 mL) and stirred at room temperature for 24 hours, then heated to 60 C for 6 hours. Water (20 mL) was added and the resulting precipitate was vacuum filtered washing with water. The isolated solid was dried under vacuum to yield 180 mg (56%) of the title compound.

III. Methods of Use of Tetrahydroindolone Derivatives and Analogues According to the Present Invention One aspect of a method of use of tetrahydroindolone derivatives and analogues according to the present invention is a method of treating or palliating cognitive/attention deficit disorders in general. For the purposes of the present invention, and not intended as a limitation, the term "cognitive/attention deficit disorders" shall include Attention Deficit Disorder (ADD), Attention Deficit Hyperactivity Disorder (ADHD), mild cognitive impairment, and dementia. These cognitive/attention deficit disorders may result from inherited factors, disease, injury or other, presently unknown physiological, anatomical, metabolic, environmental, or social factors. Moreover, the methods and compositions of the present invention are also useful as neuroprotectants. The inventors have proposed the non-limiting theory that the compounds of the present invention stimulate regeneration of mammalian neurons in the peripheral nervous system. This is accomplished by administering an effective amount of a tetrahydroindolone derivative or analogue according to the present invention to a mammal.

Another aspect of a method of use of tetrahydroindolone derivatives and analogues according to the present invention is a method of stimulating neurogenesis in the central nervous system of a mammal comprising the step of administering an effective amount of a tetrahydroindolone derivative or analogue according to the present invention to the mammal.

Yet another aspect of a method of use of tetrahydroinolone derivatives and analogues according to the present invention is a method of stimulating neuroprotection in the central or peripheral nervous system of a mammal comprising the step of administering an effective amount of a tetrahydroindolone derivative or analogue according to the present invention to the mammal.

Exemplary dosages in accordance with the teachings of the present invention for these tetrahydroindolone derivatives and analogues range from 0.0001 mg/kg to 60 mg/kg, though alternative dosages are contemplated as being within the scope of the present invention. Effective amounts (dosages) can be chosen by the treating physician by taking into account such factors as the size, weight, age, and sex of the patient, the physiological state of the patient, the severity of the condition for which the tetrahydroinolone derivative or analogue is being administered, the response to treatment, the type and quantity of other medications being given to the patient that might interact with the tetrahydroindolone derivative or analogue, either potentiating it or inhibiting it, and other pharmacokinetic considerations such as liver and kidney function.

The administration of tetrahydroindolone derivatives or analogues according to the present invention is believed to increase the level of mRNA encoding at least one neurotrophic factor in a tissue that is in chemical communication with a motor neuron or a sensory neuron. The term "chemical communication" as used herein means that at least one chemical substance that can affect the growth, differentiation, survival, or functioning of motor neurons or sensory neurons can flow from the tissue to the neuron. The neurotrophic factor stimulates the growth of neurons.

The term "effective amount" as used herein in this specification can be determined based on observations of the skilled practitioner. Compounds of the present invention can be administered to patients in need thereof using a range of dosages. The effects can then be measured for each dose and compared with patients receiving a placebo preparation. Patients demonstrating improved cognition and/or increased attention spans and/or increased attention spans coupled with decreases in observed hyperactivity will be considered to have received and "effective amount." Dosage adjustments based on weight, age and severity of symptoms are well within the skilled of the ordinary practitioner.

The present inventors have also proposed that an "effective amount" of the present compounds may or means an amount of the tetrahydroindolone derivative or analogue that causes a detectable increase in the messenger RNA level of at least one neurotrophic factors known in the art that can be measured.

Methods of measuring the mRNA levels typically involve hybridization to probes containing mRNA-specific sequences and detecting the quantity of hybrid nucleic acid formed. The hybrid nucleic acid formed is typically detected by a label incorporated in one of the two nucleic acid strands forming the hybrid. This label can be radioactive or non-radioactive; if non-radioactive, it can be fluorescent, chemiluminescent, bioluminescent, enzymatic, or can make use of another detectable property. Detection can also be performed using the polymerase chain reaction (PCR) mechanism or a variant thereof. PCR is described in detail in U.S. Pat. No. 4,683,195 to Mullis et al. and U.S. Pat. No. 4,683,202 to Mullis et al. Other detection methods, including other amplification methods, are known in the art. One particularly suitable method uses reverse transcription with MMLV reverse transcriptase followed by PCR.

Depending upon the particular needs of the individual subject involved, the tetrahydroindolone derivative or analogue according to the present invention may be administered in various doses to provide effective treatment concentrations based upon the teachings of the present invention. What constitutes an effective amount of the selected tetrahydroindolone derivative or analogue will vary based upon such factors as the activity of the selected tetrahydroindolone derivative or analogue, the physiological characteristics of the subject, the extent or nature of the subject's disease or condition, and the method of administration. Generally, initial doses will be modified to determine the optimum dosage for treatment of the particular mammalian subject. The tetrahydroindolone derivatives or analogues can be administered using a number of different routes including orally, topically, transdermally, intraperitoneal injection, or intravenous injection directly into the bloodstream. Of course, effective amounts of the tetrahydroindolone derivative or analogue can also be administered through injection into the cerebrospinal fluid or infusion directly into the brain, if desired.

The methods of the present invention can be effected using a tetrahydroindolone derivative or analogue according to the present invention administered to a mammalian subject either alone or in combination as a pharmaceutical formulation. Further, the tetrahydroindolone derivative or analogue according to the present invention can be combined with pharmaceutically acceptable excipients and carrier materials such as inert solid diluents, aqueous solutions, or non-toxic organic solvents.

Method of Testing Compounds In Vivo Using Two Animal Models

Passive avoidance is an acute memory paradigm that indicates an increased neuronal function and is an effective means for measuring changes in an animals cognition and attention. In this paradigm mice are allowed to enter a dark compartment from a lighted compartment, but are given a footshock (2 mA for 5 seconds) when they enter the dark compartment. Twenty-four hours after this training session, animals that are placed back in the lighted compartment of two compartment (light-dark) apparatus do not make the transition into the dark compartment. If an agent (30 mg/kg cycloheximide i.p. in saline) immediately after the training session is given to the animals, they will make the transition into the dark compartment (i.e. memory of the shock is lost). Compounds with suspected cognitive enhancing effects and/or causing improvements in attention span and/or decreased hyperactivity effects (positive effects) are given by i.p. administration two hours prior to the training trial in attempt to block the effects of cycloheximide. Mice that exhibit positive effects are those that avoid moving into the dark chamber. This behavioral response is defined as passive avoidance. A no effect response in this test is defined as a failure to stay in the lighted compartment for 120 seconds. Mice were selected as the animal for testing candidate compounds' effects on cognition, attention, hyperactivity and dementia due to their long history in such clinical trial. Mice, as well as other rodents including rats, have proven to be ideal laboratory animals in testing neurologically active compounds and the results obtained using rodent models correlate well with results in humans and other mammals. Moreover, results obtained from the rodent model are generally predictive of results obtained in humans and other mammals and serve as a pharmacologically acceptable basis for establishing dosages on a weight/weight basis (e.g.: mg of drug per kilogram of animal body weight). Finally, to further test the cognitive/attention span enhancing effects of the present compounds a primate model was designed. Aged primates (rhesus monkeys all greater than 21 years old) were previously trained to a set criterion. Next, Neo-339 was administered orally to the monkeys at 0.1 mg/kg, 1.0 mg/kg and 10 mg/kg. Significant levels of task improvement were observed at 1 hour and at 24 hours post drug administration (data not shown). It is understood that the present invention is intended for the treatment of all mammals in need thereof. Specifically, the mammal is a human.

Passive Avoidance Test of 4-[3-(4-Oxo-4,5,6,7-tetrahydroindolon-1-yl)propionylamino} Benzoic Acid Ethyl Ester Administered Intraperitoneally The passive avoidance test of Example 2 was used to test 4-[3-(4-oxo-4,5,6,7-tetrahydroindolon-1-yl)propionylamino} benzoic acid ethyl ester (Example 1, KA NEO 339) with intraperitoneal administration with doses ranging from 0.00001 to 10 mg/kg. The minimum effective dose (MED) is 0.001 mg/kg. (Note: it has been established that Neo-339 is metabolized into the hydroxy form known as Neo-362 See FIG. 1.)

IV. Pharmaceutical Compositions

Another aspect of the present invention is pharmaceutical compositions. A pharmaceutical composition according to the present invention comprises: (1) an effective amount of a tetrahydroindolone derivative or analogue according to the present invention as described above; and (2) a pharmaceutically acceptable carrier.

A pharmaceutically acceptable carrier can be chosen from those generally known in the art including, but not limited to, human serum albumin, ion exchangers, alumina, lecithin, buffer substances such as phosphates, glycine, sorbic acid, potassium sorbate, and salts or electrolytes such as potassium sulfate. Other carriers can be used. If desired, these pharmaceutical formulations can also contain preservatives and stabilizing agents and the like, as well as minor amounts of auxiliary substances such as wetting or emulsifying agents, as well as pH buffering agents and the like which enhance the effectiveness of the active ingredient. Other carriers can be used.

Liquid compositions can also contain liquid phases either in addition to or to the exclusion of water. Examples of such additional liquid phases are glycerin, vegetable oils such as cottonseed oil, organic esters such as ethyl oleate, and water-oil emulsions.

The compositions can be made into aerosol formations (i.e., they can be "nebulized") to be administered via inhalation. Aerosol formulations can be placed into pressurized acceptable propellants, such as dichloromethane, propane, or nitrogen. Other suitable propellants are known in the art.

Formulations suitable for parenteral administration, such as, for example, by intravenous, intramuscular, intradermal, and subcutaneous routes, include aqueous and non-aqueous isotonic sterile injection solutions. These can contain antioxidants, buffers, preservatives, bacteriostatic agents, and solutes that render the formulation isotonic with the blood of the particular recipient. Alternatively, these formulations can be aqueous or non-aqueous sterile suspensions that can include suspending agents, thickening agents, solubilizers, stabilizers, and preservatives. Compositions suitable for use in methods according to the present invention can be administered, for example, by intravenous infusion, orally, topically, intraperitoneally, intravesically, intrathecally, transdermally and combinations thereof. Formulations of tetrahydroindolone derivatives or analogues suitable for use in methods according to the present invention can be presented in unit-dose or multi-dose sealed containers, in physical forms such as ampoules or vials.

V. Conclusion

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The invention claimed is:

1. A pharmaceutical composition comprising:
a) a compound of Formula (I)

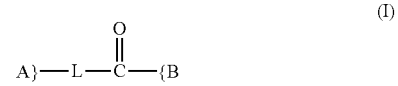

wherein
A is

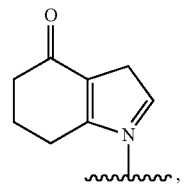

where N is bonded to L;
L is a hydrocarbyl moiety of 1 to 6 carbon atoms optionally substituted with one or more substituents selected from the group consisting of lower alkyl, amino, hydroxy, lower alkoxy, lower alkylamino, lower alkylhio, and oxo; and
B is —OZ or N(Y$_1$)-D, where Z is hydrogen or alkyl and Y$_1$ is hydrogen or alkyl which, when taken with D, can form a cyclic 5- or 6-membered saturated structure which can contain one other heteroatom which can be O, N, or S, of which N can be further substituted with Y$_2$, where Y$_2$ is alkyl, aryl, heteroaryl, aralkyl, heteroaralkyl, alkanoyl, aroyl, heteroaroyl, aralkanoyl, heteroaralkanoyl, alkylsulfonyl, arylsulfonyl, heteroarylsulfonyl, aralkylsulfonyl, heteroaralkylsulfonyl, alkoxycarbonyl, aryloxycarbonyl, heteroaryloxycarbonyl, aralkoxycarbonyl, heteroaralkoxycarbonyl, alkylaminocarbonyl, arylaminocarbonyl, heteroarylaminocarbonyl, aralkylaminocarbonyl, or heteroaralkylaminocarbonyl, in which the alkyl portions can be cyclic and can contain from 1 to 3 heteroatoms which can be N, O, or S; and b) a pharmaceutically acceptable carrier.

2. The pharmaceutical composition of claim 1, wherein L has the structure —$(CH_2)_n$— wherein n is an integer from 1 to 6.

3. The pharmaceutical composition of claim 2, wherein n is 2.

4. The pharmaceutical composition of claim 1, wherein the moiety B is $N(Y_1)$-D.

5. The pharmaceutical composition of claim 4, wherein $Y_1$ is hydrogen.

6. The pharmaceutical composition of claim 4, wherein $Y_1$ is lower alkyl.

7. The pharmaceutical composition of claim 6, wherein $Y_1$ is methyl.

8. The pharmaceutical composition of claim 1, wherein D is

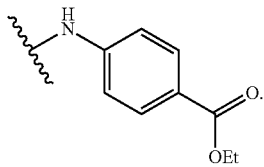 [SMILES: *Nc1ccc(C(=O)OCC)cc1]

9. The pharmaceutical composition of claim 5, wherein D is

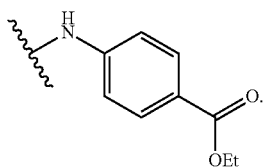 [SMILES: *Nc1ccc(C(=O)OCC)cc1]

10. The pharmaceutical composition of claim 1, wherein the pharmaceutical composition further comprises a preservative.

11. The pharmaceutical composition of claim 1, wherein the pharmaceutical composition further comprises a stabilizing agent.

12. The pharmaceutical composition of claim 1, wherein the pharmaceutical composition further comprises a wetting agent.

13. The pharmaceutical composition of claim 1, wherein the pharmaceutical composition further comprises an emulsifying agent.

14. The pharmaceutical composition of claim 1, wherein the pharmaceutical composition further comprises a buffering agent.

15. The pharmaceutical composition of claim 1, wherein the pharmaceutical composition further comprises an antioxidant.

16. The pharmaceutical composition of claim 1, wherein the pharmaceutical composition further comprises a suspending agent.

17. The pharmaceutical composition of claim 1, wherein the pharmaceutical composition further comprises a thickening agent.

18. The pharmaceutical composition of claim 1, wherein the pharmaceutical composition further comprises a solubilizer.

19. The pharmaceutical composition of claim 1, wherein the pharmaceutical composition further comprises a bacteriostatic agent.

20. The pharmaceutical composition of claim 1, wherein the pharmaceutical composition is an oral formulation.

21. The pharmaceutical composition of claim 1, wherein the pharmaceutical composition is a parenteral formulation.

22. The pharmaceutical composition of claim 1, wherein the pharmaceutical composition is a solid formulation.

23. The pharmaceutical composition of claim 1, wherein the pharmaceutical composition is a liquid formulation.

24. The pharmaceutical composition of claim 1, wherein the pharmaceutical composition is a suspension formulation.

25. The pharmaceutical composition of claim 1, wherein the pharmaceutical composition is an aerosol formulation.

26. The pharmaceutical composition of claim 1, wherein the pharmaceutical composition is an injection formulation.

* * * * *